United States Patent
Sharma et al.

(10) Patent No.: US 6,291,739 B1
(45) Date of Patent: Sep. 18, 2001

(54) **METHOD FOR SCREENING OF POTENTIAL ANTI-EPILEPTIC DRUGS USING A *DROSOPHILA MELANOGASTER* MODEL**

(75) Inventors: Abhay Sharma; Sushil Kumar, both of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/535,517

(22) Filed: Mar. 24, 2000

(51) Int. Cl.[7] .................. G01N 33/00; A01K 67/033; C12N 15/00
(52) U.S. Cl. ..................... 800/3; 800/13; 800/22
(58) Field of Search ..................... 800/3, 13, 22

(56) References Cited

PUBLICATIONS

Sharma, A. & Kumar, S. The antiepileptic drug sodium valproate affects body weight in Drosophila. Current Science 76:142–145, 1999.*

Sharma, A. & Kumar, S. Toxic and teratogenic effects of antiepileptic drugs in Drosophila. Current Science 76:476–480, 1999.*

* cited by examiner

*Primary Examiner*—Dave T. Nguyen
*Assistant Examiner*—Quang Nguyen
(74) *Attorney, Agent, or Firm*—Darby & Darby

(57) ABSTRACT

The invention relates to a method for screening anti-epileptic drugs using fruit fly *Drosophila melanogaster* by generating single and double mutant lines of $K^+$ channel genes in Drosophila melanogaster, culturing mutant lines on Drosophila medium under standard conditions, identifying the mutants, separating male flies under ether anesthesia, supplying the mutant males with medium containing each of the four antiepileptic drugs, phenobarbital, phenytoin, carbaamazepine and valproate, separately, administering ether anesthesia to the drug treated flies and examining their leg shaking intensity under stereomicroscope, observing the antiepileptic effect in the drug treated males wherein a reduced intensity of leg shaking, compared to leg shaking in normally fed etherized males, is indicative of antiepileptic activity in the drug.

2 Claims, No Drawings

METHOD FOR SCREENING OF POTENTIAL ANTI-EPILEPTIC DRUGS USING A *DROSOPHILA MELANOGASTER* MODEL

FIELD OF THE INVENTION

The present invention relates to a method for the screening of anti-epileptic drugs using an animal model. More particularly, the present invention relates to a method for the screening of anti-epileptic drugs using neurological mutants of the fruit fly *Drosophila melanogaster*.

By studying the effect of various established anti-epileptic drugs (AEDs) on neuronal hyperexcitability phenotype of these mutants, the applicants demonstrate that animal models, particularly fruit fly could serve as a simple, rapid and inexpensive whole organism in vivo phenotype-based model for screening of drugs, compounds, natural products etc. for anti-epileptic-like activities. The development of an animal model and the associated process for neuroactive drug screening is of immense value in the development and identification of drugs and their potential for treatment of neurological disorders such as epilepsy.

BACKGROUND OF THE INVENTION

Epilepsy refers to a collection of disorders affecting 1–2 % of the global population. It is a brain disorder characterized by recurrent seizures, brief changes in behaviour caused by disordered, synchronous and rhythmic firing of populations of neurons in the central nervous system. Epilepsies are caused both by genetic factors and by cortical damage. They have been classified into more than 40 distinct types on the basis of characteristic symptoms and signs, cause, seizure types, electroencephalographic patterns and age of onset. The single common feature of epilepsy syndromes is a persistent increase of neuronal excitability that occasionally and unpredictably results in a seizure. With the identification of mutations in genes encoding voltage- and ligand- gated ion channels as molecular aetiology of some forms of inherited human epilepsy, and with the understanding of altered synapse function as the causal factor in epilepsies caused by cortical damage, it has been learnt that the common mechanisms underlying the hyperexcitability in diverse forms of epilepsy is alteration of intrinsic properties of neurons and/or synaptic function (McNamara, 1999, *Nature* 399: A15–A22; Puranam and McNamara, 1999, *Curr. Op. Neurobiol.* 9: 281–287; Steinlein, 1998, *Clin. Genet.* 54: 169–175).

In many epileptic patients, seizures can be controlled with the established AEDs such as phenobarbital, phenytoin, carbamazepine and valproate (Brodie and Dichter, 1996, *N. Eng. J. Med* 334: 168–175; Marson and Chadwick, 1996, *Curr. Op. Neurol* 9:103–106). However, around 25–30 % of patients continue to have seizures despite optimal therapy and others have unacceptable side effects (Brodie and Dichter, 1996, *N. Eng. J. Med* 334: 168–175). In recent years, a number of new AEDs such as gabapentin, lamotrigine, felbamate and clobazam have been developed (Macdonald and Grenfield, 1997, *Curr. Op. Neurobiol.* 10: 121–128). Adequate data on the possible teratogenic effects of these AEDs, however, is not available. In addition, these new drugs have limited efficacy and have the potential for serious side effects. Clinical trials have shown that some patients respond to one drug in a better way than to another, even when they have similar types of seizures and the drugs used have similar mechanisms of action; the frequency and severity of side effects also vary substantially. In view of the above, it is clear that there is a need to develop more AEDs.

As with other human disease research, epilepsy research has been dependent upon the use of animal models, notably in the screening of thousands of compounds for possible anticonvulsant activity. AEDs that are commonly used to treat generalized epilepsies in humans have been shown to respond to animal models of epilepsy (Batini et al, 1996, *Trends Neuosci.* 19: 246–252). Putnam and Merritt (1937, *Science* 85: 525–526) were the first to show that an experimental model of epilepsy could be used to screen chemical compounds systematically for anticonvulsant activity. Since then the search for new AEDs has followed three approaches (Laird II, 1985, *FASEB* 44: 2627–2628). The majority of the currently used AEDs were discovered by the first approach in which new chemical entities synthesized as potential AEDs are screened for anticonvulsant efficacy using classical experimental models (electroshock and chemoshock) of epilepsy. The second approach has been to search for the molecular mechanism(s) by which clinically effective anticonvulsant agents work so that more efficacious and selective agents may be developed. In the third, information derived from an understanding of the molecular defect(s) responsible for the epileptic state has formed the basis of drug development.

Evaluation of anticonvulsant activity is possible at various biological levels such as subcellular, cellular, cerebral and spinal neuronal, whole brain, normal intact animal and modified intact animal (Swinyard and Kupferberg, 1985, *FASEB* 44: 2629–2633). Methods like receptor pharmacology in vitro, single neuron recording in vitro and in vivo, electrophysiology, neurochemistry, histochemistry, electroencephalography etc. are used for the study of anticonvulsant activity. Many of these methods are highly valuable, particularly for differentiating drug mechanisms and as penultimate tests before clinical study of potential AEDs. Many of them are however time-intensive and expensive. They are therefore not suitable for routine use in the screening for anticonvulsant agents. It is clear that there is a need to develop new models. These models should be validated by testing against the prototype AEDs.

In the fruit fly *Drosophila melanogaster*, several mutations in genes encoding voltage- and ligand- gated ion channels and genes involved in synaptic function are known (Brunner and O'Kane, 1997, *Trend Genet.* 13: 85–87; Lindsley and Zimm, 1992, The Genome of Drosophila melanogaster, Acad. Press; Wu and Bellen, 1997, *Curr. Op. Neurobiol.* 7: 624–630; Zhou et al, 1999, *Neuron* 22: 809–818). Some of these mutations produce behavioral hyperexcitability in flies. Of particular interests are the $K^+$ channel mutants Shaker (Sh), Hyprkinetic (Hk) and ether a go-go (eag) whose most distinctive phenotype is a rapid leg shaking under ether anesthesia (Choumnard et al, 1995, *Proc. Natl. Acad. Sci. USA* 92: 6763–6767; Ganetzky, 1989, *Genetics* 21 : 201–204; Kaplan and Trout, 1968, *Genetics* 61: 399–409). Voltage-dependent $K^+$ channels are conserved from bacteria to man (Baumann et al, 1988, *EMBO J.* 7: 2457–2463; Doyle et al, 1998, *Science* 280: 69–77; Doyle and Stubbs, 1998, *Trends Genet.* 14: 92–98; MacKinnon et al, 1998, *Science* 280: 106–108 Stansfeld et al, 1997, *Trends Neurosci.* 20: 13–14; Trudeau et al, 1995, *Science* 269: 92–95; Wang et al, 1998, *Science* 282: 1890–1893). Prompted by the finding that a human counterpart of Drosophila $K^+$ channel gene is mutated in a human epilepsy (Biervert et al, 1998, *Science* 274: 403–406; Singh et al, 1998, *Nature Genet.* 18: 25–29), and fascinated by the simple, quick and inexpensive method of visualizing neuronal hyperexcitability phenotype in Sh, Hk and eag flies (Ganetzky, 1989, *Genetics* 21: 201–204), we attempted to evaluate these mutants as a model to screen drugs, compounds, natural products etc. for antiepiletic-like activities. Most of the established AEDs act by preventing repetitive firing of action potentials in depolarized neurons through voltage- and use- dependent blockade of $Na^+$ channels (Brodie and Dichter, 1996, *New Eng. J. Med.* 334: 168–175; Macdonald and Greenfield, 1997, *Curr. Op. Neurobiol.* 10: 121–128; Rogawsky and Porter, 1990, *Pharmacol. Rev.* 42: 223–286). The knowledge that a relatively minor reduction of $K^+$ current may produce epilepsy, and the possibility that a drug modestly enhancing the $K^+$ current could effectively inhibit seizures (McNamara, 1999, Nature 399: A15–A22), further strengthened our idea of evaluating $K^+$ channel mutants of *Drosophila melanogaster* as a phenotype-based whole organism in vivo model for antiepileptic drug screening. Extensive literature is available on genetics, behavioral biology, molecular biology, electrophysiology and neurobiology of many of the mutants we studied (Cha et al, 1999, *Nature* 402: 809–813; Chen et al, 1996, *Neuron* 17: 535–542; Doyle and Stubbs, 1998, *Trends Genet.* 14: 92–98; Ganetzky, 1989, *Genetics* 21: 201–204; Glauner et al, *Nature* 402: 813–817; Iverson et al, 1988, *Proc. Natl. Acad. Sci. USA* 85 5723–5727; Kamb et al, 1987, *Cell* 50: 405–413; Kreusch et al, 1998, *Nature* 392 945–948; Lichtinghagen et al, 1990, *EMBO J.* 9: 4399–4407; Papazian et al, 1987, *Science* 237: 749–753; Pongs, 1992, *Physiol Rev.* 72: S69–S88; Salkoff and Wyman, 1981, *Nature* 293: 228–230; Salkoit 1983, *Nature* 302: 249–251; Starace et al, 1997, *Neuron* 19: 1319–1327; Tempel et al, 1987, *Science* 237: 770–775; Timpe et al, 1988, *Nature* 331: 143–145). So far, however, neither any suggestion nor any attempt has been made to either evaluate or use these mutants for antiepileptic drug screening. To the best of our knowledge, only two reports, both authored by us, exist on the effects of AEDs on Drosophila (Sharma and Kumar, 1999, *Curr. Sci.* 76: 142–145; Sharma and Kumar, 1999, *Curr. Sci.* 76: 476–480). These reports however do not include any suggestion and/or result on usefulness of the mutant flies in screening for antiepileptic-like activities.

OBJECTS OF THE INVENTION

The main object of the invention is the development of an animal model for the identification of antiepileptic-like agents.

It is an object of the invention to develop a method for screening of anti-epileptic drugs using an animal model.

It is a further object of the invention to develop a method for the screening of anti-epileptic drugs using fruit fly *Drosophila melanogaster*.

It is another object of the invention to develop a simple, inexpensive and rapid method for the screening of anti-epileptic drugs.

It is a further object of the invention to develop an ethical animal model for the screening of anti-epileptic drugs that is also rapid, simple and inexpensive.

SUMMARY OF THE INVENTION

Accordingly the present invention provide s a method f or the screening of anti-epileptic drug s using fruit fly, *Drosophila melanogaster*, said method comprising (a) generating s ingle and double mutant lines of $K^+$ channel genes in *Drosophila melanogaster*

(b) culturing mutant lines on Drosophila medium under standard conditions (c) identifying the mutants as dark body colour males as opposed to nonmutant light body colour females (d) separating male flies under ether anesthesia (e) supplying the mutant males with medium containing each of the four antiepileptic drugs, phenobarbital, phenytoin, carbamazepine and valproate, separately at a dose ranging between 2–4 mg/ml, depending upon the drug used, for 16–20 hrs. at 20±2° C.

(f) administering ether anesthesia to the drug treated flies and examining their leg shaking intensity under stereomicroscope (g) observing the antiepileptic effect in the drug treated males wherein a reduced intensity of leg shaking, compared to leg shaking in normally fed etherized males, is indicative of antiepileptic activity in the drug.

In one embodiment of the invention, the mutants used are selected from a group consisting of C (1) DX, yf/$Sh^3$; C (1) DX, yf/$Sh^5$; C (1) DX, yf/$Sh^6$; C (1) DX, yf/$Sh^{14}$; C (1) DX, yf/$eag^1$; C (1) DX, yf/$Hk^1$; C (1) DX, yf/$Sh^3$ $eag^1$; C (1) DX, yf/$Sh^5$ $eag^1$; C (1) DX, yf/$Sh^6$ $eag^1$; C (1) DX, yf/$Sh^{14}$ $eag^1$; C (1) DX, yf/$Sh^3$ $Hk^1$; C (1) DX, yf/$Sh^5$ $Hk^1$; C (1) DX, yf/$Sh^6$ $Hk^1$; C (1) DX, Yf/$Sh^{14}$ $Hk^1$; C (1) DX, yf/$eag^1$ $Hk^1$.

In another embodiment of the invention, the anti-epileptic drugs used are selected from a group consisting of phenobarbital sodium, phenytoin sodium, carbamazepine and sodium valproate.

Accordingly, the invention provides a simple, inexpensive and rapid method of using $K^+$ channel mutants of the fruit fly *Drosophila melanogaster* as a biological screen for antiepileptic-like drug testing wherein the agents to be screened could be fed to mutant flies with characteristic leg shaking behaviour under ether anesthesia followed by searching for a decrease in ether induced leg shaking intensity indicative of an antiepileptic-like agent. The mutants of the fruit fly *D. melanogaster* may be selected from the single gene mutants $Sh^5$, $Sh^6$, $Sh^{14}$, $eag^1$ and $Hk^1$, and the double mutants $Sh^3$ $eag^1$, $Sh^5$ $eag^1$, $Sh^6$ $eag^1$, $Sh^{14}eag^1$, $Sh^3$ $Hk^1$, $Sh^5Hk^1$, $Sh^6$ $Hk^1$, $Sh^{14}$ $Hk^1$ and $eag^1Hk^1$.

DETAILED DESCRIPTION OF THE INVENTION

Mutants and Drugs Used

To evaluate Drosophila $K^+$ channel mutants as a drug screening model, various established AEDs were administered to them and the resulting behavioral phenotype was observed. Since Drosophila $K^+$ channel genes as well as $K^+$ channel genes involved in human epilepsy are known to form both homo- and hetero- meric channels (Chen et al, 1996, *Neuron* 17: 535–542; Chouinard et al, 1995, *Proc. Natl. Acad. Sci. USA* 92: 6763–6767; Kamb et al, 1987, *Cell* 50: 405413; Kim et al, 1997, *J. Neurosci.* 17: 8213–8224; McNamara, 1999, *Nature* 399: A15–A22; Schroeder et al, 1998, *Nature* 396: 687–690; Wang et al, 1998, *Science* 282: 18901893), we also evaluated various double mutant combinations. As described below, a total of 15 lines were generated and tested. The mutants examined were $Sh^3$, $Sh^5$, $Sh^6$, $Sh^{14}$, $eag^1$, $Hk^1$, $Sh^3$ $eag^1$, $Sh^5$ $eag^1$, $Sh^6$ $eag^1$, $Sh^{14}$ $eag^1$, $Sh^3$ $Hk^1$, $Sh^5$ $Hk^1$, $Sh^6$ $Hk^{14}$ $Sh^{14}$ $Hk^1$ and $eag^1$ $Hk^1$. The flies were administered the four AEDs, phenobarbital sodium (PB), phenytoin sodium (PHT), carbamazepine (CBZ) and sodium valproate (VAL), separately, and then the intensities of their leg shaking under ether anesthesia were recorded. As described below, the behavioral hyperexcitability in most of the mutant lines was found to be reduced by one or the other AED. However, the number of drugs doing so most effectively was maximum in case of $Sh^5$ and $Sh^5$ $eag^1$. As normal (without drug treatment) level of ether-induced leg shaking is higher in $Sh^5$ $eag^1$ than $Sh^5$, we observed that AED-induced suppression of behavioral hyperexcitability is most easily and effectively detected in $Sh^5$ $eag^1$. We therefore validaed the use of voltage-gated $K^+$ channel mutants of *Drosophila melanogaster* as a simple, rapid and inexpensive whole organism im vivo phenotype-based model for screening of drugs, compounds, natural products etc. for antiepileptic-like activities.

Construction and Culture of Mutant Lines

The mutant lines generated and tested are listed below. Standard methods of Drosophila genetics were used for the purpose. Only males harbour the neurological mutations. Unaffected females having compound X-chromosomes can be easily distinguished from males because of yellow body colour marker in them. The starting materials used in generating the following lines were obtained from Bowling Green Stock Centre, USA ($Sh^3$, stock number # 1194, Bloomington Stock Centre, USA ($Sh^5$, #111; $Sh^{14}$, #3563; $Hk^1$, #3562) and Umea Stock centre, Sweden ($eag^1$, #22255).

1. C (1) DX, yf/$Sh^3$
2. C (1) DX, yf/$Sh^5$
3. C (1) DX, yf/$Sh^6$
4. C (1) DX, yf/$Sh^{14}$
5. C (1) DX, yf/$eag^1$
6. C (1) DX, yf/$Hk^1$
7. C (1) DX, yf/$Sh^3$ $eag^1$
8. C (1) DX, yf/$Sh^5$ $eag^1$
9. C (1) DX, yf/$Sh^6$ $eag^1$
10. C (1) DX, yf/$Sh^{14}$ $eag^1$
11. C (1) DX, yf/$Sh^3$ $Hk^1$
12. C (1) DX, yf/$Sh^5$ $Hk^1$
13. C (1) DX, yf/$Sh^6$ $Hk^1$
14. C (1) DX, yf/$Sh^{14}$ $Hk^1$
15. C (1) DX, yf/$eag^1$ $Hk^1$ Standard Drosophila manipulation methods were followed. Cultures were grown on a medium containing maize a powder, sugar, ye and Nipagin at 20±2° C. Culture conditions were kept identical for all the lines. Special precautions, such as minimum exposure to ether etc., were taken during handling of neurological mutants.

Double mutants, known to exhibit synergistic interaction (Chouinard et al, 1995, *Proc. Natl. Acad Sci. USA* 92: 6763–6767), were generated using standard methods of Drosophila genetics. Sh, Hk and eag are all X-linked genes. $Sh^3$ $eag^1$, for example, was constructed as follows. A single $Sh^3$ male was crossed to a single virgin $eag^1$ female. Parents were removed after egg. collection. Several $F_1$ males and females were allowed to mate among themselves. The eggs were collected and flies removed. $F_2$ males were separated from $F_2$ females. More than three hundred $F_2$ males were then screened for flies exhibiting an unusually higher level of ether-induced leg shaking. This followed a test in which three male flies, one each of $Sh^3$, $eag^1$ and the product of above screening, were together subjected to ether anesthesia. The flies included in the test were all grown, aged and manipulated identically. For identification, wings of three types of flies were gently marked with a unique colour using marking pens. The leg shaking intensity of the flies were then visually estimated by simultaneously observing them under a stereomicroscope. Several sets of flies were examined in this manner. And each set was repeatedly tested several times, after appropriate intervals. Only those putative double mutants were confirmed as true $Sh^3$ $eag^1$ who passed the test each time it was repeated. Each of these confirmed double mutant males were then crossed to one C (1) DX, yf female each. $F_1$ males from each pair mating were once again separately checked for enhanced ether-induced leg shaking activity, compared to identically grown, aged and handled C (1) DX, yf/$Sh^3$ and C (1) DX, yf/$eag^1$, as described earlier. Finally, a single line of $Sh^3$ $eag^1$ was retained. In this manner, single lines of each of the 15 mutants were raised.

Drug Treatment

Ten to 15 days old optimally grown male flies of a given line were pooled together and starved for 4–5 hrs at 20±2° C., before being shifted to vials containing 0.5 ml of either normal food (N.F.) or food containing a single AED @ 4 mg/ml PB, 2.5 mg/ml PHT and 2 mg/ml CBZ and VAL. Food was poured as follows. A set of five vials, containing 5 ml food each, was kept in a boiling water bath. Just after the food was melted, food from one vial was used to prepare N.F. vials. The rest four vials were quickly used for preparing PB, PHT, CBZ and VAL vials. A thorough mixing of drug was ensured. After 4–6 hrs of their preparation, vials were used for treating flies. Normally, 20 flies were treated in a vial. Vials were kept 20±2° C. for 16–20 hrs in an inverted position, i.e., food side up, following which leg shaking assay was performed. Identical conditions were maintained for all the lines at all the steps.

Observing the Effect of Drugs on Mutant Phenotype

Drug treated flies were individually exposed to ether vapour as per standard procedure. Their leg shaking behaviour was then observed under a stereomicroscope.

Flies were etherized in a 75 mm glass vial with approximately 800 mg of absorbant cotton as plug. 0.2 ml of diethyl ether was used for each round of anesthesia, duration of which was approximately 1.5 min, at 23±3° C. During etherization, the vial was gently shaken continuously so that flies remained at the bottom of the vial throughout. All the flies were etherized and further manipulated identically. The intensity of leg shaking for any given fly strain was determined visually and recorded on a scale of 4. For fixing the scale, a separate group of 10–12 flies treated with N.F. were together etherized and observed first. The flies exhibiting maximum intensity of leg shaking in the group were cosidered to have leg shaking intensity of 4. Comparison of leg shaking intensities between strains was not attempted, except that between $Sh^5$ and $Sh^5$ $eag^1$ (for reason mentioned later). In case of these two mutants, leg shaking intensities of flies fed on normal food were also recorded on a scale of 4. Scale was fixed for this purpose using $Sh^5$ $eag^1$ flies.

As presented in Table 1, all the AEDs except CBZ affected behavioral hyperexcitability in mutant flies. Considering the inherent inaccuracy in the subjective method of scoring leg shaking intensities by visual estimation, the test of significance applied at 0.1% level of confidence (t<0.001) would be expected to show practically most useful mutants for drug screening purpose. Under this condition, the behavioral hyperexcitability was found to be reduced by PB in $Sh^3$, $Sh^5$, $Sh^6$, Hk, $Sh^3$ $eag^1$, $Sh^5$ $eag^1$, $Sh^3$ $Hk^1$ and $Sh^5$ $Hk^1$; by PHT in $Sh^5$, $Sh^6$, $eag^1$, $Sh^5$ $eag^1$, $Sh^6$ $eag^1$ and $Sh^3$ $Hk^1$; by VAL in $Sh^5$ and $Sh^5$ $eag^1$. It is clear it leg shaking activities of $Sh^5$ and $Sh^5$ $eag^1$ are suppressed by maximum number of drugs. These two mutants therefore appear to be the best choice for drug screening model. However, when drug treatment experiment was repeated with $Sh^5$ and $Sh^5$ $eag^1$, we found that AED-induced suppression of leg shaking was more obvious in the later than the former. Normally grown Sh eag double mutants exhibit an enhanced level of leg shaking due to a synergistic interaction (Lindsley and Zimm, 1992, The Genome of *Drosophila melanogaster*, Acad. Press). After recording leg shaking intensities of 10 normally grown $Sh^5$ and $Sh^5$ $eag^1$ flies each on a scale of 4, we obtained the values (Mean ±S.E.) of 2.9±0.17 and 3.8±0.13 respectively. It is therefore this enhancement (t<0.001) of leg shaking in the double mutant that results in an easy detection of AED-induced reduction in their behavioral hyperexcitability. We therefore conclude that among all the 15 mutant strains studied, $Sh^5$ $eag^1$ is the best possible biological screen for testing drugs, compounds, natural products etc. for antiepileptic-like activities.

TABLE 1

Leg shaking intensities (Mean ± S.E.) after ether anesthesia

| Food/Drugs → Mutants ↓ | N.F | PB | PHT | CBZ | VAL |
|---|---|---|---|---|---|
| $Sh^3$ | $ | $ | $ | $ | $ |
| $Sh^5$ | 3.72 ± 0.10 (25) | 1.84 ± 0.12 (25)* | 2.96 ± 0.16 (25)* | 3.92 ± 0.08 (25) | 2.68 ± 0.18 (25)* |
| $Sh^6$ | 3.77 ± 0.14 (9) | 1.66 ± 0.23 (9)* | 2.33 ± 0.33 (9)* | 3.77 ± 0.14 (9) | 3.11 ± 0.30 (9)* |
| $Sh^{14}$ | 3.50 ± 0.21 (10) | 2.20 ± 0.36 (10)* | 2.30 ± 0.34 (10)* | 3.70 ± 0.20 (10) | 2.60 ± 0.29 (10)* |
| $eag^1$ | 3.80 ± 0.10 (15) | 3.10 ± 0.19 (15)* | 1.86 ± 0.25 (15)* | 3.80 ± 0.10 (15) | 3.60 ± 0.15 (15) |
| $Hk^1$ | 3.80 ± 0.12 (10) | 2.60 ± 0.25 (10)* | 2.40 ± 0.35 (10)* | 3.80 ± 0.12 (10) | 3.20 ± 0.31 (10) |
| $Sh^3\ eag^1$ | 3.60 ± 0.20 (10) | 2.30 ± 0.14 (10)* | 3.10 ± 0.22 (10) | 3.30 ± 0.31 (10) | 3.20 ± 0.31 (10) |
| $Sh^5\ eag^1$ | 3.80 ±0.10 (25) | 1.96 ± 0.17 (25)* | 2.76 ± 0.22 (25)* | 3.88 ± 0.06 (25) | 2.88 ± 0.12 (25)* |
| $Sh^6\ eag^1$ | 3.75 ± 0.12 (20) | 2.47 ± 0.21 (20)* | 2.10 ± 0.29 (20)* | 3.80 ± 0.09 (20) | 3.35 ± 0.18 (20) |
| $Sh^{14}\ eag^1$ | 3.77 ± 0.14 (9) | 3.22 ± 0.36 (9) | 2.66 ± 0.37 (9)* | 3.88 ± 0.11 (9) | 3.44 ± 0.28 (9) |
| $Sh^3\ Hk^1$ | 3.70 + 0.20 (10) | 2.30 ± 0.23 (13)* | 1.71 ± 0.28 (7)* | 3.72 ± 0.19 (11) | 3.20 ± 0.34 (10) |
| $Sh^5\ Hk^1$ | 3.57 ± 0.13 (14) | 3.15 ± 0.18 (13)* | 3.38 ± 0.13 (13) | 3.66 ± 0.12 (15) | 3.60 ± 0.12 (15) |
| $Sh^6\ Hk^1$ | 3.53 ± 0.12 (15) | 3.20 ± 0.19 (10) | 2.92 ± 0.13 (13)* | 3.50 ± 0.13 (14) | 3.53 ± 0.12 (15) |
| $Sh^{14}\ Hk^1$ | 3.60 ± 0.20 (10) | 1.90 ± 0.26 (10)* | 2.70 ± 0.28 (10)* | 3.70 ± 0.14 (10) | 3.50 ± 0.25 (10) |
| $eag^1\ Hk^1$ | 3.71 ± 0.18 (7) | 3.28 ± 0.28 (7) | 2.28 ± 0.42 (7)* | 3.57 ± 0.20 (7) | 2.42 ± 0.48 (7)* |

$indicates nonavailability of data due to practical difficulty in estimating very weak leg shaking characteristic of $Sh^3$ mutation. Numbers in parentheses indicate numbers of flies examined.
*indicates significant ($t < 0.05$ to $< 0.001$) reduction in leg shaking activity compared to N.F. Abbreviations and other details are as described in the text.

ADVANTAGES OF THE INVENTION

1. Compared to conventional antiepileptic drug screening using animal models such as genetically epilepsy-prone rat, the fruit fly model described here is simple, inexpensive and rapid
2. Using Drosophila flies for drug research is currently not unethical from animal rights point of view

What is claimed is:

1. A method for screening potential anti-epileptic drugs using fruit fly Drosophila melanogaster which comprises:
   (a) generating single and double mutant fly lines of K+ channel genes in Drosophila melanogaster,
   (b) culturing the mutant fly lines of step (a) on Drosophila medium under standard conditions,
   (c) selecting the dark body mutant fly males of step (b) as opposed to nonmutant light body colour females,
   (d) separating the male mutant flies of step (c) under ether anesthesia,
   (e) supplying the mutant males of step (d) with medium containing a potential antiepileptic drug at a dose ranging between 2–4 mg/ml, depending upon the drug used, for 16–20 hrs at 20±2° C.,
   (f) administering ether anesthesia to the drug treated flies of step (e) and examining their leg shaking intensity under stereomicroscope, and
   (g) observing the anti-epileptic effect in the drug treated flies of step (f) wherein a reduced intensity of leg shaking, compared to leg shaking in normally fed etherized flies of step (d), is indicative of potential anti-epileptic activity in the drug.

2. The method of claim 1, wherein the mutant fly lines used are selected from the group consisting of C (1) DX, yf/$Sh^3$; C (1) DX, yf/$Sh^5$; C (1) DX, yf/$Sh^6$; C (1) DX, yf/$Sh^{14}$; C(1) DX, yf/$eag^1$; C (1) DX, yf/$Hk^1$; C (1) DX, yf/$Sh^3\ eag^1$; C(1) DX, yf/$Sh^5\ eag^1$; C (1) DX, yf/$Sh^6\ eag^1$; C (1) DX, yf/$Sh^{14}\ eag^1$; C (1) DX, yf/$Sh^3\ Hk^1$; C (1) DX, yf/$Sh^5\ Hk^1$; C (1) DX, yf/$Sh^6\ Hk^1$; C (1) DX, yf/$Sh^{14}Hk^1$ and C (1) DX, yf/$eag^1\ Hk^1$.

* * * * *